United States Patent [19]

Daftary

[11] Patent Number: 5,073,111

[45] Date of Patent: Dec. 17, 1991

[54] ANATOMICAL RESTORATION DENTAL IMPLANT SYSTEM

[76] Inventor: Fereidoun Daftary, 5015 Orrville, Woodland Hills, Calif. 91367

[21] Appl. No.: 424,901

[22] Filed: Oct. 20, 1989

[51] Int. Cl.$^5$ ............................................. A61C 8/00
[52] U.S. Cl. ..................................... 433/173; 433/174
[58] Field of Search ............... 433/172, 173, 174, 175, 433/176, 192, 193, 194, 204

[56] References Cited

U.S. PATENT DOCUMENTS

| | | |
|---|---|---|
| 3,576,074 | 4/1971 | Gault et al. |
| 3,618,212 | 11/1971 | Weissman |
| 3,934,347 | 8/1973 | Lash et al. |
| 4,252,525 | 2/1981 | Child .................... 433/173 |
| 4,416,629 | 11/1983 | Mozsary et al. ............ 433/174 |
| 4,552,532 | 11/1985 | Mozsary ................ 433/173 |
| 4,636,216 | 1/1987 | Tatum ..................... 623/16 |
| 4,657,510 | 4/1987 | Gittleman ............... 433/173 |
| 4,713,003 | 12/1987 | Symington et al. ........ 433/173 |
| 4,722,688 | 2/1988 | Lonca ................... 433/173 |
| 4,744,755 | 5/1988 | Ross .................... 433/173 |
| 4,758,160 | 7/1988 | Ismail .................. 433/173 |
| 4,780,080 | 10/1988 | Harris .................. 433/173 |
| 4,789,337 | 12/1988 | Scortecci ............... 433/173 |
| 4,854,872 | 8/1989 | Detsch .................. 433/173 |
| 4,856,994 | 8/1989 | Lazzara et al. .......... 433/173 |
| 4,872,839 | 10/1989 | Brajnovic ............... 433/173 |
| 4,906,191 | 3/1990 | Soderberg ............... 433/173 |

FOREIGN PATENT DOCUMENTS

| | | | |
|---|---|---|---|
| 0291103 | 11/1988 | European Pat. Off. ............ 433/174 |
| 0323421 | 7/1989 | European Pat. Off. ............ 433/173 |
| 2413883 | 9/1975 | Fed. Rep. of Germany ...... 433/173 |
| 3711884 | 10/1988 | Fed. Rep. of Germany ...... 433/173 |
| 8903200 | 4/1989 | PCT Int'l Appl. ................. 433/173 |

Primary Examiner—Cary E. O'Connor
Attorney, Agent, or Firm—Thomas I. Rozsa

[57] ABSTRACT

A system and method is provided for implanting tooth analogues in the jawbone resulting in aesthetically and functionally desirable gingival tissue contours after restoration. The system permits modification and adaptation of the tooth analogue to meet intraoral demands in a manner similar to that used in the preparation and restoration of natural teeth. The system comprises a standard fixture and cover screw passed through opened gingival tissue and implanted in the jawbone. After the osseointergration of the fixture, the gingiva is reopened, the cover screw removed and a healing cap having a predetermined contour, is attached to the fixture. The reopened gingiva re-heals in a shape determined by the contour of the healing cap. The healing cap is then removed and replaced by an abutment having an emergence profile matching that of the healing cap. An immediate snug fit between the gingival tissues and the abutment is thereby provided at the time of connection of the abutment to the fixture. A crown is removably attached to the abutment by a screw extending through the side of the crown into the abutment.

24 Claims, 4 Drawing Sheets

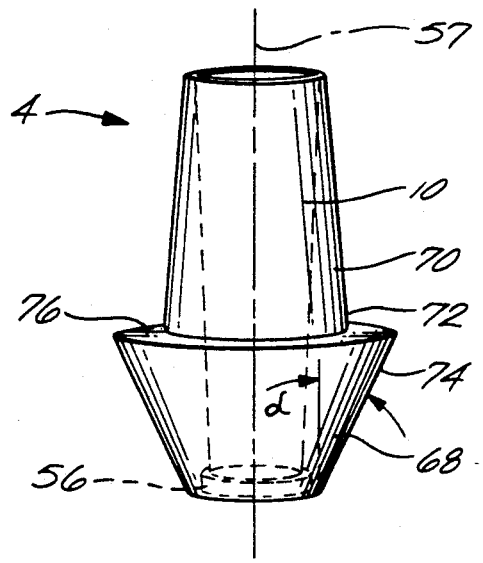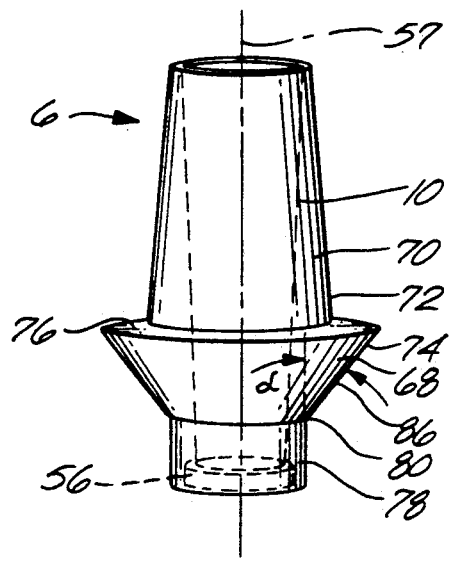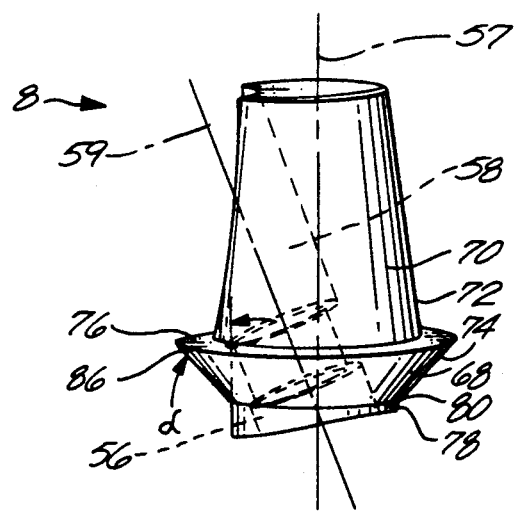

ANATOMICAL RESTORATION DENTAL IMPLANT SYSTEM

FIELD OF THE INVENTION

The present invention relates generally to the field of dental implants and in particular to a system providing a tooth analogue and a gingival tissue healing cap which results in a restoration having tissue-implant profiles similar to that of a natural tooth and its surrounding gingiva.

BACKGROUND OF THE INVENTION

Many systems have been proposed for rigidly fixing metal or ceramic materials to the alveolus of a human mandible or maxilla in an effort to provide a long term replacement for lost teeth. Early systems were successful for only limited periods of time and were eventually rejected as foreign bodies Later systems, as described by Sneer U.S. Pat. No. 3,589,011, Brainin U.S. Pat. No. 3,797,113, Taylor U.S. Pat. No. 3,979,828, Reuther et al. U.S. Pat. No. 4,324,550, and Mozsary et al. U.S. Pat. No. 4,416,679, have proven to offer long term success by providing rigid anchorage in the supporting bone. Intraoral restoration of such osseointegrated devices has been accomplished with many different systems that modified the original attempts. Such modifications have been described in Harras U.S. Pat. No. 4,780,080, Symington et al. U.S. Pat. No. 4,713,003, and Gittlemen U.S. Pat. No. 4,657,510. However, these restorative systems have required biologic and aesthetic compromises. The interface between an implant and its surrounding gingival tissue is often insufficiently close to prevent food and bacteria from entering this area. Such foreign matter can cause chronic infection and bone loss, resulting in eventual loss of the implant. Implants in current use have a round root form dimensionally different from that of a normal tooth root morphology. This makes aesthetic restoration difficult and impedes the development of a natural soft gingival tissue contour.

There exists a need for a dental implant system providing an implant root and gingival tissue interface having an improved resistance to bacterial infection and providing a contour more nearly approximating that of a natural tooth and its surrounding tissue.

SUMMARY OF THE INVENTION

The invention provides a system and a method for implanting tooth analogues in the alveolus of the jawbone. The emergence profile of the analogue more closely matches that of a natural root and the system provides a tight fit between the analogue and the gingiva upon installation of a crown or other tooth replacement.

The system comprises an implantable fixture having proximal and distal end portions, the proximal end portion having means for being implanted through opened gingival tissue into the alveolus of the jaw bone, the distal end portion being accessible from the outer surface of the jaw bone. The fixture contains a hollow interior beginning with an opening in the distal end portion and extending towards the proximal end portion. The hollow has threads along at least a portion of its length.

The invention utilizes a cover screw for sealing the hollow portion of the fixture during the time the jaw bone is growing about the fixture. After osseointegration of the fixture, the gingiva is reopened and the cover screw is removed and replaced by a healing cap. The healing cap provides a predetermined contour to the re-healing gingival tissue. The healing cap has a stem having proximal and distal end portions, a frusto-conical segment having larger and smaller ends, a cylindrical segment having proximal and distal ends, and a screw head segment having a proximal end and a driven end. The proximal end portion of the stem is threaded within the hollow of the implantable fixture. The distal end portion of the stem is attached to the smaller end of the frusto-conical segment. The larger end of the frusto-conical segment is attached to the proximal end of the cylindrical segment. The distal end of the cylindrical segment is attached to the screw head segment. The driven end of the screw head segment is cooperable with a driving tool, such as a screwdriver. The axis of all the segments are in alignment with the axis of the stem.

After the re-opened gingival tissue has healed about the healing cap, the healing cap is removed and replaced with a hollow abutment having the same contour as that of the healing cap. Having the same contour permits the abutment to tightly fit the healed opening in the gingival tissue upon engagement of the abutment with the fixture. The abutment is removably affixed to the fixture by a screw having a threaded end portion and a driven end portion. The threaded end portion is passed through the abutment and threaded in the hollow of the fixture. The driven end portion of the screw is cooperable with a driving tool, such as a screwdriver and engages the abutment, holding the abutment in place against the fixture.

In a presently preferred embodiment, the abutment comprises a divergent segment and a head segment, the segments both having a frusto-conical shape. The smaller end of the divergent segment engages distal end portion of the fixture, while the larger end of the divergent segment is attached to the smaller end of the head segment. The smaller end of the head segment being smaller than the larger end of the divergent segment creates a shoulder at their juncture. The axis of the divergent and head segments are in alignment with the axis of the fixture.

The system additionally comprises a tooth analogue releasibly engagable with the abutment. In a presently preferred embodiment the analogue comprises a crown having a hollow interior adapted to fit on the head section of the abutment The crown additionally has an opening extending laterally through the sidewall thereof. The opening is alignable with the threaded hollow in the side of the abutment. A holding screw secures the crown to the abutment. The screw has a threaded end portion and a driven end portion. The threaded end portion is passed through the opening in the side of the crown and is threaded in the opening in the side of the abutment. The driven end portion cooperable with a driving tool and is engagable within a recess in the sidewall of the crown. With the exception of the crown, all elements of the invention are made of titanium or other rigid substance, compatible with implantation within the body.

The foregoing and other advantageous and distinguishing features of the invention are described in detail below and are recited in the appended claims.

BRIEF DESCRIPTION OF THE DRAWINGS

FIGS. 7-9 are side elevation views of preferred abutments of the present invention.

DETAILED DESCRIPTION

Figure 1:
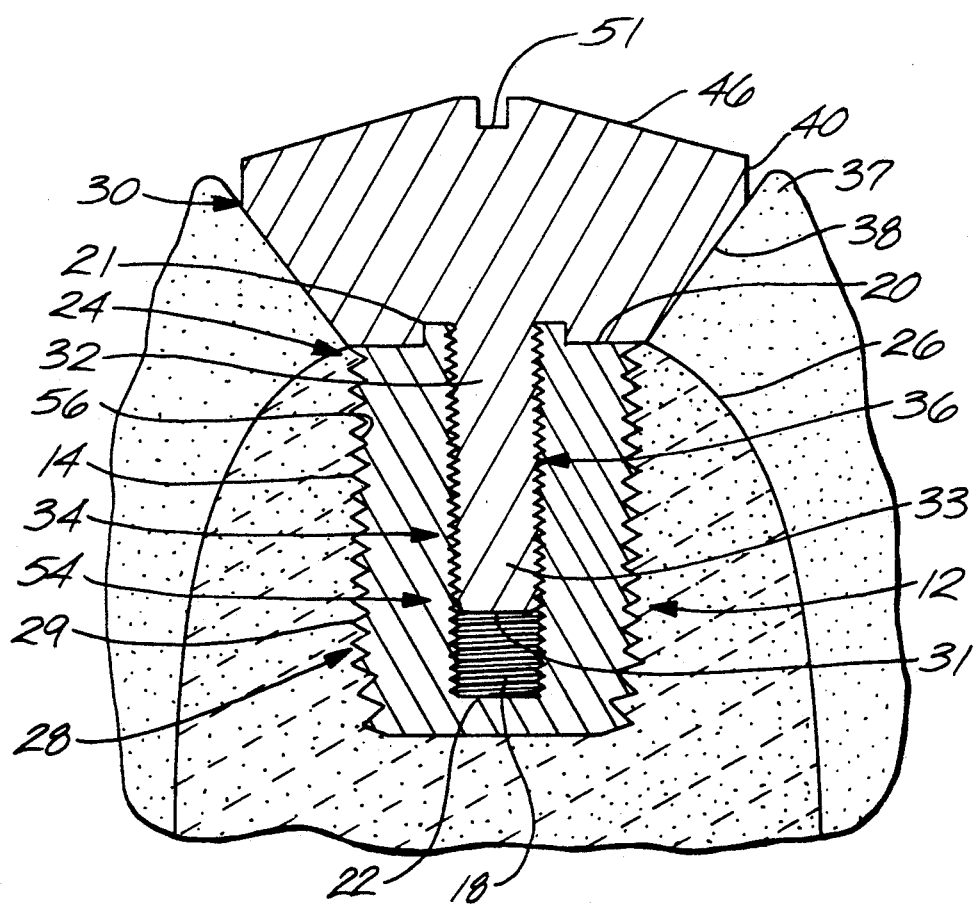
FIG. 1 is a sectional view of a healing cap and fixture of a presently preferred embodiment of the invention showing a portion of the jawbone and gingiva in a broken away configuration.
Figure 2:
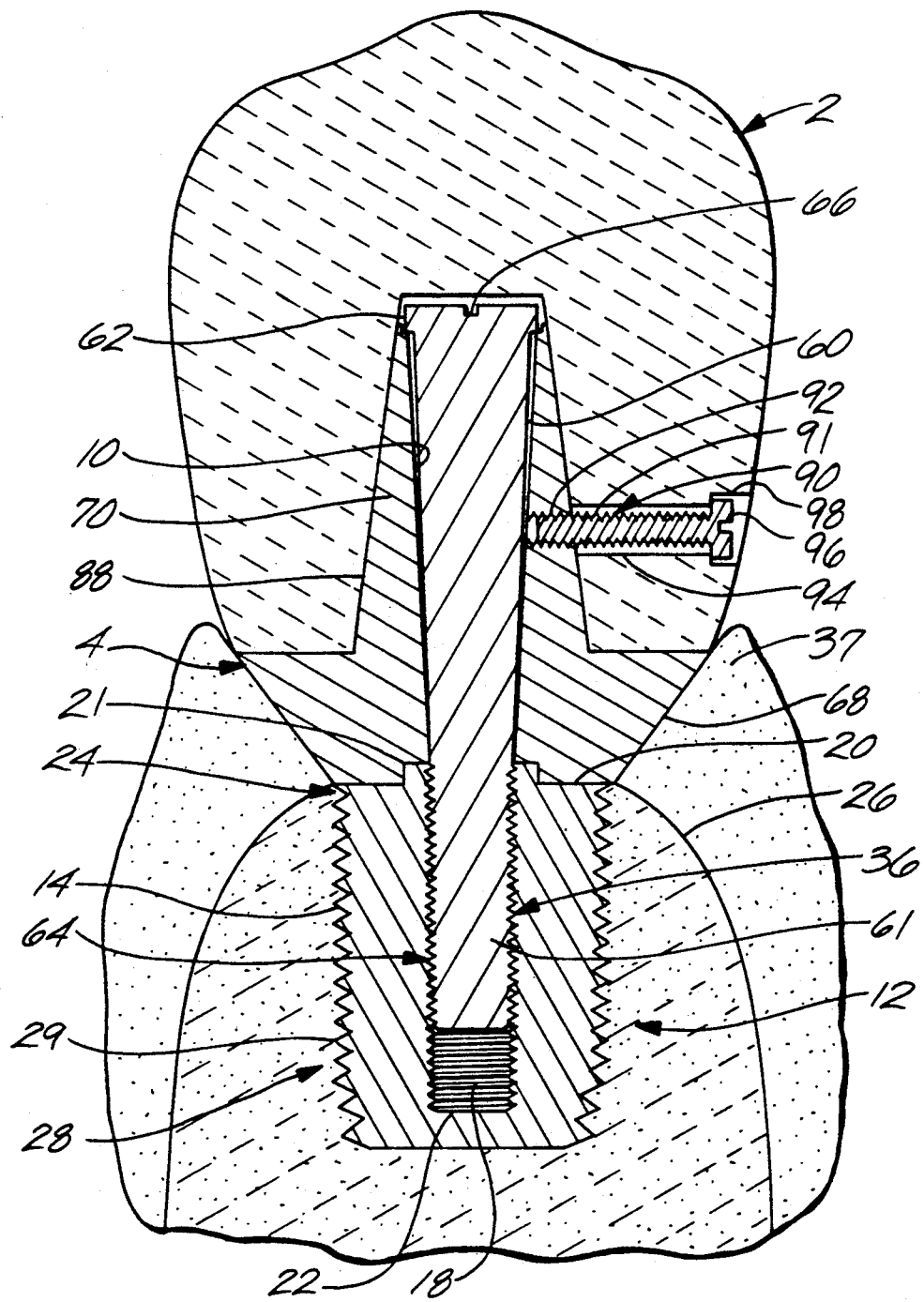
FIG. 2 is a sectional view of a crown, abutment, fixture and holding screws of the presently preferred embodiment of the invention showing a portion of the jawbone and gingiva in a broken away configuration.

Referring now to FIGS. 1 & 2, the present invention is a method and a system of providing a tooth analogue for one or more missing teeth. The tooth analogue may comprise a crown, a fixed or removable partial denture, or a fixed or removable full denture. In a presently preferred embodiment of the invention the analogue comprises a crown 2 removably affixed to an abutment 4. According to the preferred method of installing the analogue in the mouth of a patient, a socket is prepared in the alveolus of the jawbone where a tooth has been extracted or otherwise lost. A conventional fixture 12 is implanted in this area. An exemplary fixture is roughly cylindrical in shape and possesses a threaded surface 14. The fixture 12 includes a hollow portion 18 which extends from the upper surface 20 of the fixture toward the lower surface 22 thereof. The fixture is implanted such the distal end portion 24 of the fixture extends to the outer surface of the jaw bone 26. The proximal end portion 28 of the fixture extends into the jaw bone 26 as far as is necessary for a satisfactory implantation. In one embodiment, the jawbone is drilled and threaded in preparation for receiving the fixture. During implantation, the threaded surface 14 of the fixture 12 threadingly engages the threaded surface of the jaw bone 29.

After implantation of the fixture 12, a cover screw is threaded into the fixture (not shown) to seal it during the period in which bone is growing about the proximal portion 28 of the fixture. The gingival tissue 37 above the fixture is closed according to procedures well known in the art. Upon completion of osseointergration of the fixture 12, the gingival tissue 37 above the fixture is reopened and the cover screw is removed. The healing cap 30 is then threaded into the fixture and held in place by a stem 31. The stem has a distal end portion 32, and a proximal end portion 33, which together have a threaded surface 34. The threaded surface 34 is engaged with a threaded surface 36 within the hollow portion 18 of the fixture to hold the healing cap 30 in place. The fixture 12 has a raised lip 21 around the opening of the hollow 18 in the distal end portion 24 of the fixture. The lip 21 may be circular or hexagonal in shape. The lip fits within an appropriately configured socket 39 of the healing cap 30. The engagement of the lip within the socket provides additional support to the engagement of the healing cap 30 to the fixture 12.

The healing cap 30 is additionally configured to allow the gingival tissues 37, surgically displaced during removal of the cover screw to heal around the cap in a shape which is dimensionally similar to the tooth previously removed or lost. The proper contouring of the gingival tissues 37 during their healing is necessary to assure a tight fit between the abutment and the gingiva. This tight fit provides resistance to food particles and bacterial infection and provides improved esthetics for the completed restoration.

Referring additionally now to FIGS. 3-6, preferred healing caps 30 may be configured in differing diameters, heights and emergence profiles to permit the gingival tissues 37 to be guided in healing to a proper form, commensurate with that desired at the completion of the restoration.

Figure 3:
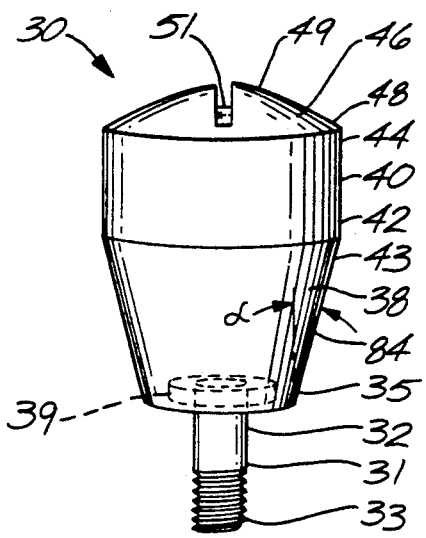
FIGS. 3-6 are side elevation views of preferred healing caps of the present invention.
Figure 4:
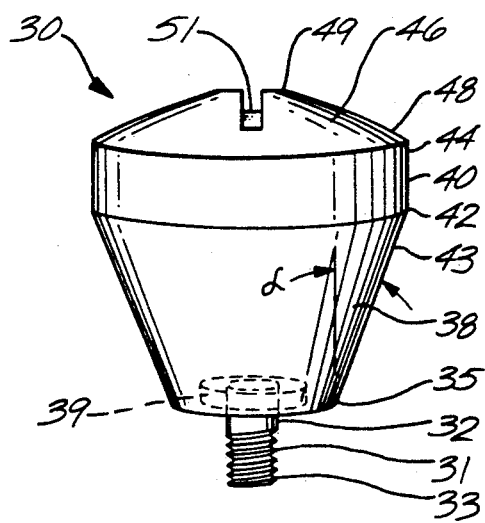

Details of three section healing caps 30 are shown in FIGS. 3 & 4. The caps have a frusto-conical section 38, the smaller end 35 of which is attached to the distal end 32 of the stem 31. A cylindrical section 40 extends away from the frusto-conical section 38, having a proximal end 42 attached to the larger end 43 of the frusto-conical section. A screw head segment 46 terminates the healing cap 30, having a proximal end 48 which is attached to the distal end 44 of the cylindrical section 40. The screw head segment 46 also has a driven end 49 cooperable with a driving tool. The driven end is preferably a slot 51 transverse to the long axis of the healing cap 30, which may be driven by a blade screwdriver.

Figure 5:
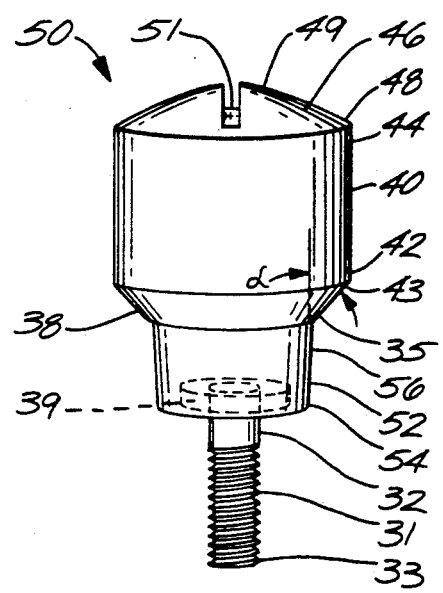
Figure 6:
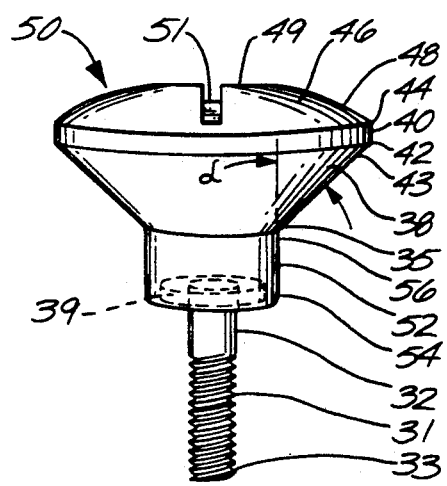

Four section healing caps 50 are shown in FIGS. 5 & 6. These caps have the same elements as the three section caps 30 with the addition of a cylindrical shaped base 52. The base 52 is used to fill the space between the surface of the jaw bone and the distal portion 24 of the fixture 12 when the surface of the jaw bone, after healing about the fixture, extends above the distal portion of the fixture. The base 52 has a proximal end portion 54 and a distal end portion 55. The proximal end portion 54 is attached to the distal end portion 32 of the stem 31, and the distal end portion 55 is attached to the smaller end 35 of the frusto-conical section.

The long axes of the segments 38, 40, 46, 52 and the stem 31 of the healing caps 30, 50 are preferably aligned.

At the juncture of the segments 52, 38, 40 & 46, the circumference of each segment is preferably the same as that of each adjoining segment.

The healing caps 30 & 50 are preferably made of a one piece construction.

After placement of the fixture 12 in the jaw bone 26 and a healing cap 30, 50 through the gingival tissue 37, the gingiva is sutured about the cap. The fixture and cap are permitted to remain in place until a tooth analogue has been made and is ready for insertion into the fixture. This requires a period of eight weeks or longer. When the tooth analogue is ready for insertion the cap is removed from the fixture 12 and replaced with a tooth analogue including an abutment 4, 6, or 8.

Referring now to FIGS. 2, & 7-9 abutments 4, 6 & 8 are provided having different emergence profiles, in harmony with those of the healing caps 30, 50.

The abutment 4, 6, 8 has a socket 56 adapted to fit the lip 21 on the distal end portion 24 of the fixture 12. The engagement of the lip 21 and the socket 56 provides resistance to shear forces resulting from mastication. Referring to FIGS. 7 & 8, the abutments 4 & 6 have a hollow 10, extending from the socket 56, through the interior of the fixture, centered about the long axis 57 of the abutments 4 & 6. As shown in FIG. 9, a hollow 58 of the abutment 8 is symmetrical about an axis 59 offset from the long axis 57 of the abutment. The offset of the hollow 58 is selected to accommodate a malaligned implanted fixture, or to aid in paralleling abutments for fixed partial dentures. The hollow 58 may emerge partially or fully from the sidewall of the abutment.

Referring again to FIG. 2, the abutment 4 is secured to the fixture 12 by a screw 60 having a threaded end portion 61 and a driven end portion 62. The screw is passed through the abutment hollow 10 and engaged with the threaded surface 36 within the fixture 12. The driven end portion 62 of the screw 60 is preferably a slot 66, transverse to the long axis of the screw, which is cooperable with a blade screwdriver.

Referring now to FIGS. 7–9, the abutments 4, 6, & 8 are comprised of a divergent segment 68, and a head segment 70, both segments having a frusto-conical shape. The larger end 72 of the head segment 70 is affixed to and extends outward from the larger end 74 of the divergent segment 68. The larger end 74 of the divergent segment 68 is larger than the larger end 72 of the head segment 70 thereby creating a shoulder 76 at their juncture. This shoulder provides a surface through which chewing forces from the crown 2, or other tooth analogue, are transferred to the abutment 4, 6, 8.

The abutments 6 & 8 additionally comprise a cylindrically shaped base 78, as shown in FIGS. 8 & 9. The base is joined to and extends away from the smaller end 80 of the divergent segment 68. The end 82 of the base 78 is normal to the axis of the hollow 10, 58.

The long axes 57 of the abutments 7, 8 & 9 are preferably in alignment, and the base 78 and the divergent segment 68 are preferably of the same circumference at their juncture. The abutments 4, 6, 8 are preferably made of a one piece construction.

To provide the best fitting of the gingival tissues 37 with the abutment 4, 6, 8, the sidewall 84 of the frusto-conical segment of the healing cap 30, 50 and the sidewall 86 of the divergent segment 68 of the abutment, preferably extend outward from the smaller end of the segments at an angle, angle α as shown in FIGS. 3, 7 & 8, of between 45° and 65° to the long axis of the segment.

A feature of the use of a screw 60 to secure the abutment 4, 6, 8 to the fixture 12 is that the divergent segment 68 can be prepared in the same manner as a natural tooth, with reduction of the occlusal, and proximal surfaces of the abutment as necessitated by the situation. Additionally, axial reduction of the abutment may be performed to facilitate fabricating anatomically correct restorations. Axial reduction also permits separation from adjacent teeth or implants, and varying cervical contours as required for tissue health and aesthetic appearance.

Referring again to FIG. 2, the crown 2 is comprised of elements well known in the dental arts. The crown 2 has a hollow interior 88 adapted to fit on the head 70 of the abutment 4. The crown 2 may be releasably attached to the abutment by a dental crown adhesive or by a screw. When the screw attachment method is used, a screw 90 is passed through an aperture 91 in the side of the crown. The abutment 4 has a threaded hollow 92 in its sidewall extending into the hollow 10 of the abutment. The screw 90 comprises a threaded end portion 94 and a driven end portion 96. The screw is passed through the aperture 91 and the threaded end portion 94 is engaged in the threaded hollow 92. The side of the crown additionally has a recess 98 which receives the driven end portion 96.

With the exception of the crown 2, all elements of the invention are preferably fabricated of pure titanium, but may be made of other biocompatible materials.

The dental implant system of the present invention provides for development of proper gingival tissue form resulting in more aesthetically and functionally desirable tissue contours at the time of and following tooth analogue connection. The system also allows modification and adaptation of the abutment 4, 6, 8 to meet intraoral demands in a manner similar to that used in the preparation and restoration of natural teeth. In view of the foregoing description of the invention in accordance with the requirements of the patent statutes, those skilled in the relevant arts will have no difficulties making changes and modifications in the different described elements of the invention in order to meet their specific requirements or conditions. For example, those elements having a driven end may comprise a socket cooperable with an allen wrench. Multiple as well as single restorations may be accomplished. Fixed full or partial dentures or removable prostheses may constitute the tooth analogues. Such changes and modifications may be made with out departing from the scope and spirit of the invention as set forth in the following claims.

What is claimed is:

1. A dental implant system implantable in the gingival tissue and the alveolus of the jaw bone comprising:
    an implantable fixture having proximal and distal end portions, the proximal end portion having means for being embedded in opened gingival tissue and the alveolus of the jaw gone, the distal end portion being accessible from the outer surface of the jaw bone, the fixture being made of a substance permitting healing of the opened gingival tissue and growth of the jaw bone about the fixture, the fixture further including a hollow extending from an opening in the distal end portion towards the proximal end portion, the hollow having threads along at least a portion of its length;
    means for sealing the hollow portion of the fixture during a period after implantation in which the jaw bone is growing about the proximal portion of the fixture;
    means for providing a predetermined contour to the gingival tissue adjacent the distal end of the fixture opened for the removal of the sealing means, such that the gingival tissue re-heals in a contour reverse to that of the contour of said means;
    a tooth analogue;
    abutment means for supporting the tooth analogue, engagable with the implantable fixture and having the same contour as the fixture sealing and gingival tissue contouring means, such that the abutment means makes a tight fit with the healed gingival tissue adjacent the distal end of the fixture; and
    means for releasibly attaching the tooth analogue to the abutment means.

2. The dental implant system of claim 1 wherein the tooth analogue comprises a crown having a hollow interior adapted to fit on a portion of the abutment.

3. The dental implant system of claim 2 wherein the means for releasibly attaching the crown to the abutment comprises:
    a threaded hollow in the side of the abutment means;
    an opening extending laterally through the side of the crown, the crown opening alignable with the threaded hollow in the side of the abutment means;
    a holding screw having a threaded end portion and a driven end portion, the threaded end portion passing through the opening in the side of the crown and threaded in the opening in the side of the abutment, the driven end portion cooperable with a driving tool and engagable with the crown.

4. The dental implant system of claim 1 wherein the contour means comprises a healing cap, the healing cap comprising:
   a stem having proximal and distal end portions, the proximal end portion being threadable within the hollow of the implantable fixture;
   a frusto-conical segment, the smaller end of the segment being attached to distal end of the stem, with the axis of the segment being in alignment with the axis of the stem;
   a cylindrical segment having proximal and distal ends, the proximal end being attached to the larger end of the frusto-conical segment, with the axis of the cylindrical segment being in alignment with the axis of the frusto-conical segment; and
   a screw head segment having a proximal end and a driven end, the driven end cooperable with a driving tool, the proximal end being attached to the distal end of the cylindrical segment, with the axis of the screw head segment being in alignment with the axis of the frusto-conical segment.

5. The dental implant system of claim 4 wherein said healing cap additionally comprises a base, the base having a cylindrical shape with proximal and distal ends, the proximal end of the base being attached to the distal end portion of said stem, and the distal end of the base being attached to the smaller end of said frusto-conical segment, with the axis of the base being in alignment with the axes of said stem and said frusto-conical segment.

6. The dental implant system of claims 4 or 5 wherein the exterior of the sidewall of said frusto-conical segment of said healing cap extends outward from the smaller end of the segment at an angle of between 45 degrees and 65 degrees to the axis of the segment.

7. The dental implant system of claims 4 or 5 wherein at the juncture between said screw head segment and said cylindrical segment of said healing cap, the circumference of said cylindrical segment is the same as the circumference of said screw head segment.

8. The dental implant system of claims 4 or 5 wherein at the juncture between said cylindrical segment and said frusto-conical segment of said healing cap, the circumference of said cylindrical segment is the same as the circumference of said frusto-conical segment.

9. The dental implant system of claim 1 wherein the abutment means comprises a hollow abutment device and a screw, the screw having a threaded end portion and a driven end portion, the threaded end portion passable through the abutment device and threaded in the hollow of the implantable fixture, the driven end portion cooperable with a driving tool and engagable with the abutment device.

10. The dental implant system of claim 9 wherein said hollow abutment device of said abutment means comprises:
   a. a divergent segment having a hollow frusto-conical shape, the smaller end of the segment being engagable with the distal end portion of the implantable fixture, with the axis of the segment being in alignment with the axis of the fixture; and
   b. a head segment having a hollow frusto-conical shape, the larger end of the head segment being attached to the larger end of the divergent segment, with the axis of the head segment being in alignment with the axis of the divergent segment, and the larger end of the divergent segment being larger than the larger end of the head segment thereby creating a shoulder at their juncture.

11. The dental implant system of claim 10 wherein said hollow abutment device further comprises a cylindrically shaped base attached to and extending away from the smaller end of said divergent segment, with the axis of the base being in alignment with the axis of said divergent segment.

12. The dental implant system of claim 11 wherein the axes of the hollow and said base of said hollow abutment device are offset from the axis of said abutment device such that the hollow at least partially emerges from the sidewall of said head segment and the unattached end of said base is normal to the offset axis of the hollow.

13. The dental implant system of claims 10, 11 or 12 wherein the exterior of the sidewall of said divergent segment of said hollow abutment device extends outward from the smaller end of the segment at an angle of between 45 degrees and 65 degrees to the axis of the segment.

14. The dental implant system of claim 1 wherein the means for releasibly attaching the tooth analogue to the abutment includes an adhesive.

15. A healing cap for use with an implantable fixture having an open end and a threaded hollow, the healing cap comprising:
   a stem having proximal and distal end portions, the proximal end portion being threadable within the hollow of the implantable fixture thereby sealing the fixture;
   a divergent segment having a frusto-conical shape, the smaller end of the segment being attached to distal end of the stem, with the axis of the segment being in alignment with the axis of the stem;
   a cylindrical segment having proximal and distal ends, the proximal end being attached to the larger end of the divergent segment, with the axis of the cylindrical segment being in alignment with the axis of the divergent segment; and
   a screw head segment having a proximal end and a driven end, the driven end cooperable with a driving tool, the proximal end being attached to the distal end of the cylindrical segment, with the axis of the screw head segment being in alignment with the axis of the divergent segment.

16. The healing cap of claim 15 additionally comprising a base, the base having a cylindrical shape with proximal and distal ends, the proximal end of the base being attached to the distal end portion of the stem, and the distal end of the base of the base being attached to the proximal end of the divergent segment, with the axis of the base being in alignment with the axes of the stem and the divergent segment.

17. The healing cap of claims 15 or 16 wherein the exterior of the sidewall of the divergent segment extends outward from the smaller end of the segment at an angle of between 45° and 65° to the axis of the segment.

18. The healing cap of claims 15 or 16 wherein, at the juncture between said screwhead segment and the cylindrical segment, the circumference of said cylindrical segment and said cylindrical segment is the same as the circumference of said screwhead segment.

19. The healing cap of claims 15 or 16 wherein, at the juncture of the cylindrical segment and the frusto-conical segment, the circumference of the cylindrical segment and the circumference of the frusto-conical segment are the same.

20. A method for implanting a tooth in the gingival tissue and the alveolus of the jawbone comprising:

implanting a fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from the distal end portion toward the proximal end portion, the hollow being threaded along at least a portion of its length;

sealing the hollow portion of the fixture with a cover screw during a period after implantation in which the jaw bone is growing about the proximal portion of the fixture and the opened gingival tissue is healing, thereby preventing the jaw bone from entering the fixture;

reopening the gingival tissue and removing the cover screw, replacing the screw with a healing cap which provides a predetermined contour to the gingival tissue adjacent the distal end of the fixture after the jaw bone has grown about the proximal portion of the fixture, thereby causing the gingival tissue to re-heal in a contour reverse to that of the healing cap provided;

unsealing the hollow portion of the fixture by removal of the healing cap;

engaging an abutment means for supporting a tooth analogue with the implanted fixture, the abutment means having the same contour as the healing cap such that the abutment means makes a tight fit with the gingival tissue adjacent the distal end of the fixture; and releasibly attaching a tooth analogue to the abutment means.

21. A hollow abutment for supporting a tooth analogue, the abutment engagable with an implantable fixture by means of a screw passes through the abutment, the abutment comprising:

a. a divergent segment having a hollow, a proximal end and a distal end, with the axis of the segment being in alignment with the axis of the fixture;

b. a cylindrically shaped base attached to and extending away from the proximal end of said divergent segment, with the axis of the base being in alignment with the axis of said divergent segment; and c. a head segment having a hollow, a proximal end and a distal end, the proximal end of the head segment being attached to the distal end of the divergent segment, with the axis of the head segment being in alignment with the axis of the divergent segment, and the hollow of said divergent segment being in alignment with the hollow of the head segment such that both of said hollows receive said screw, and the distal end of the divergent segment being larger than the proximal end of the head segment thereby creating a shoulder at their juncture.

22. The abutment of claim 21 wherein the axes of the hollow and said base are offset from the axis of said abutment such that the hollow at least partially emerges from the sidewall of said head segment and the unattached end of said base is normal to the offset axis of the hollow.

23. The abutment of claims 21 or 22 wherein the exterior of the sidewall of said divergent segment of said hollow abutment extends outward from the proximal end of the segment at an angle of between 45 degrees and 65 degrees to the axis of the segment.

24. The abutment of claim 21 further having a threaded side opening, and further including a tooth analogue comprising:

a. a crown having proximal and distal end portions, the distal end portion formed in the shape of the surface of a tooth, the proximal end portion having a hollow interior adapted to fit over and cooperate with said head segment of said abutment, the proximal end portion additionally having an opening extending laterally through the sidewall thereof, the opening alignable with the threaded opening in the side of said abutment; and b. a holding screw having a threaded end portion and a driven end portion, the threaded end portion passable through the opening in the side of said crown and threadable in the side opening of said abutment, and the driven end portion cooperable with a driving tool and engagable with the crown.

* * * * *